(12) United States Patent
Hancke (10) Patent No.: US 10,722,492 B2
(45) Date of Patent: Jul. 28, 2020

(54) ANDROGRAPHOLIDE TREATS PROGRESSIVE FORMS OF MULTIPLE SCLEROSIS

(71) Applicants: INNOBIOSCIENCES, LLC, Bradenton, FL (US); PHARMACEUTICAL PATENT ATTORNEYS, LLC, Morristown, NJ (US)

(72) Inventor: Juan O. Hancke, Valdivia (CL)

(73) Assignee: Inno Bioscience, LLC, Bradenton, FL (US)

( * ) Notice: Subject to any disclaimer, the term of this patent is extended or adjusted under 35 U.S.C. 154(b) by 0 days.

(21) Appl. No.: 15/774,604

(22) PCT Filed: Jun. 8, 2017

(86) PCT No.: PCT/US2017/036463
§ 371 (c)(1),
(2) Date: May 9, 2018

(87) PCT Pub. No.: WO2017/214346
PCT Pub. Date: Dec. 14, 2017

(65) Prior Publication Data
US 2019/0083458 A1 Mar. 21, 2019

Related U.S. Application Data

(60) Provisional application No. 62/347,218, filed on Jun. 8, 2016.

(51) Int. Cl.
| | | |
|---|---|---|
| *A61K 31/365* | (2006.01) | |
| *A61K 38/21* | (2006.01) | |
| *A61K 9/20* | (2006.01) | |
| *A61P 25/28* | (2006.01) | |
| *A61K 31/015* | (2006.01) | |
| *A61K 31/341* | (2006.01) | |
| *A61K 31/7048* | (2006.01) | |
| *A61K 36/19* | (2006.01) | |

(52) U.S. Cl.
CPC .............. *A61K 31/365* (2013.01); *A61K 9/20* (2013.01); *A61K 31/015* (2013.01); *A61K 31/341* (2013.01); *A61K 31/7048* (2013.01); *A61K 36/19* (2013.01); *A61K 38/21* (2013.01); *A61P 25/28* (2018.01)

(58) Field of Classification Search
CPC .................................................. A61K 31/365
See application file for complete search history.

(56) References Cited

U.S. PATENT DOCUMENTS

| | | | | |
|---|---|---|---|---|
| 8,084,495 | B2 * | 12/2011 | Hancke Orozco | ..... A61K 36/19 514/473 |
| 9,060,994 | B2 * | 6/2015 | Hancke Orozco | ... A61K 31/341 |
| 2006/0057107 | A1 * | 3/2006 | Shaked | .................. A61K 38/21 424/85.7 |
| 2014/0301981 | A1 * | 10/2014 | Hancke Orozco | ... A61K 31/341 424/85.6 |

OTHER PUBLICATIONS

Carcamo, Claudia, "IB-MS decreases disability progression in patients with progressive forms of multiple sclerosis. A double blind placebo controlled study", ECTRIMS Online Library, 2016, p. 1-2.
"Experimental autoimmune encephalomyelitis", Wikipedia, 2020, p. 1-6.
Hancke, Juan, "Efficacy, Safety and Tolerability of Andrographolides Versus Placebo in Patients With Progressive Forms of MS", NIH U.S. National Library of Medicine ClinicalTrials.gov, 2014, p. 1-10.
Marcus, Koch W., "Treatment trials in progressive MS—current challenges and future directions", Nat. Rev. Neurol., 2013, p. 496-503, V9.
Ontaneda, Daniel, "Progressive multiple sclerosis: prospects for disease therapy, repair, and restoration of function", Lancet, 2017, p. 1357-1366, V389.
Rommer, Paulus S., "Management of Secondary Progressive Multiple Sclerosis: Prophylactic Treatment—Past, Present, and Future Aspects", Multiple Sclerosis and Related Disorders, 2013, p. 241-258, V15.
Anderson, O. et al, "Multicentre, randomised, double blind, placebo controlled phase III study of weekly, low dose, subcutaneous interferon beta-1a in secondary progressive multiple sclerosis", J Neurol Neurosurg Psychiatry, 2004, p. 706-710, V7, I5.
Cadavid, D. et al, "Efficacy analysis of opicinumab in relapsing multiple sclerosis: the Phase 2b SYNERGY trial", ECTRIMS Online Library, 2016, p. 1-2, Abstract 192.
Campbell, E. et al, "Physiotherapy rehabilitation for people with progressive Multiple Sclerosis: a systematic review", Physiotherapy for progressive MS, 2016, p. 1-38.
Hawker, K. et al, "Rituximab in Patients with Primary Progressive Multiple Sclerosis Results of a Randomized Double-Blind Placebo-Controlled Multicenter Trial", Ann Neurol, 2009, p. 460-471, V66.
Kapoor, R. et al, "Lamotrigine for neuroprotection in secondary progressive multiple sclerosis: a randomised, double-blind, placebo-controlled, parallel-group trial", Lancet Neurol, 2010, p. 681-688, V9.
Panitch, H. et al, "Interferon beta-1b in secondary progressive MS Results from a 3-year controlled study", Neurology, 2004, p. 1788-1795, V63.

(Continued)

*Primary Examiner* — Yong S. Chong
(74) *Attorney, Agent, or Firm* — Pharmaceutical Patent Attorneys, LLC (57) ABSTRACT

Andrographolide 240 mg/day orally is the first treatment shown to significantly benefit progressive forms of Multiple Sclerosis in human patients.

6 Claims, 11 Drawing Sheets

(56) References Cited

OTHER PUBLICATIONS

Steiner, D. et al, "Natalizumab versus placebo in patients with secondary progressive multiple sclerosis (SMPS): Results from ASCEND, a multicenter, double-blind, placebo-controlled, randomized phase 3 clinical trial", Neurology, 2016, V87, Pe22.

Wolinsky, J.S. et al, "Glatiramer Acetate in Primary Progressive Multiple Sclerosis: Results of a Multinational, Multicenter, Double-Blind, Placebo-Controlled Trial", Ann Neurol, 2007, p. 14-24, V61.

Zajicek, J. et al, "Effect of dronabinol on progression in progressive multiple sclerosis (CUPID): a randomised, placebo-controlled trial", Lancet Neurol, 2013, p. 857-865, V12.

* cited by examiner

ANDROGRAPHOLIDE TREATS PROGRESSIVE FORMS OF MULTIPLE SCLEROSIS

RELATED APPLICATIONS

This application is the United States National Stage of Patent Cooperation Treaty application Serial No. PCT/US17/36463, filed 8 Jun. 2017, which in turn claims priority from U.S. Provisional patent application Ser. No. 62/347,218 filed 8 Jun. 2016, the contents of which are incorporated here by reference.

GOVERNMENT INTEREST

None.

PARTIES TO A JOINT RESEARCH AGREEMENT

Certain of this research has been conducted at Pontificia Universidad Catolica de Chile, pursuant to an agreement between Pontificia Universidad Catolica de Chile and the Applicant/Assignee.

SEQUENCE LISTING

None.

PRIOR DISCLOSURES BY A JOINT INVENTOR

A joint inventor is co-author of Bertoglio, J. C. et al., *Andrographis paniculata Decreases Fatigue In Patients With Relapsing-Remitting Multiple Sclerosis,* 16:77 BMC Neurology (23 May 2016).

BACKGROUND

Multiple Sclerosis (MS) is a chronic neuron-inflammatory demyelinating disorder of the Central Nervous System (CNS) that predominantly affects young adults in their 20s or 40s and is one of the most common causes of non-traumatic disability among young and middle-aged people. MS-related health care costs are estimated to be more than $10 billion annually in the United States, and $15 billion worldwide.

As of 2008, between 2 and 2.5 million people are affected globally with rates varying widely in different regions of the world and among different populations. MS affects more than 350,000 people in the United States and 2.5 million worldwide. In the United States, prevalence estimates are approximately 90 per 100,000 population.

MS symptoms can start anywhere between 10 and 80 years of age, but they usually begin between 20 and 40 years, with a mean age of 32 years. Women outnumber men by a ratio of 2-3 to 1, although in Primary Progressive MS (PPMS) the ratio is closer to equal, The name multiple sclerosis refers to scars (sclera—better known as plaques or lesions) in particular in the white matter of the brain and spinal cord. The etiology of MS is unknown. It is believed to be an autoimmune disease, in which the body's immune system attacks its own tissues. In MS, this process destroys myelin, the fatty substance that coats and protects nerve fibres in the brain and spinal cord. When myelin is damaged, the messages that travel along that nerve may be slowed or blocked. MS is characterized by areas of de-myelinated plaques disseminated throughout the CNS with a predilection for optic nerves, spinal cord, periventricular white matter (WM), corpus callosum, and cortical and sub-cortical grey matter (GM).

Later in the disease course, gradual progression of disability is observed. The overt progression of disability (secondary progressive MS) occurs when on-going irreversible tissue injury exceeds a critical threshold beyond which the nervous system can no longer compensate. At this point, the disease becomes essentially a degenerative process, with neurologic deterioration independent of on-going inflammation.

Multiple sclerosis is also known as "disseminated sclerosis" or "encephalomyelitis disseminate". It is an inflammatory disease in which the insulating covers of nerve cells in the brain and spinal cord are damaged. This damage disrupts the ability of parts of the nervous system to communicate, resulting in a wide range of signs and symptoms, including physical, mental, and sometimes psychiatric problems, While the cause is not clear, the underlying mechanism is thought to be either destruction by the immune system or failure of the myelin-producing cells. Proposed causes for this include genetics and environmental factors such as infections. MS is usually diagnosed based on the presenting signs and symptoms and the results of supporting medical tests.

MS can be classified by the comparative severity of symptoms over time. Where new symptoms occur in isolated attacks, this is termed the "relapsing-remitting" form of MS. Relapsing Remitting (RRMS) is the most common form of the disease (85% of patients), wherein symptoms appear for several days to weeks, after which they usually resolve spontaneously.

Where new symptoms build up or become more severe over time, this is termed a "progressive" form of MS. Between attacks, symptoms may disappear completely; however, permanent neurological problems often occur, especially as the disease advances. Patients with progressive forms of MS have a markedly worse clinical outlook than do patients with a relapsing-remitting form. The present invention relates to pharmaceutical compositions for treating progressive forms of MS, and more particularly to treating Secondary Progressive (SP) and Primary Progressive (PP) forms of MS.

There is no known cure for multiple sclerosis. Treatments attempt to improve function after an attack and prevent new attacks. Medications used to treat MS while modestly effective can have adverse effects and be poorly tolerated. Many people pursue alternative treatments, despite a lack of evidence of efficacy. The long-term outcome is difficult to predict. Life expectancy is 5 to 10 years lower than that of an unaffected population. Above-average outcomes are more often seen in women, those who develop the disease early in life, and those who initially experienced few attacks. In the following paragraphs, an analysis is made of the 8 drugs that have been evaluated so far, in clinical trials for various prior art treatments for MS.

After tissue damage accumulates over many years, 50% of RRMS patients typically evolve to show Secondary Progressive MS (SPMS), in which pre-existing neurologic deficits gradually worsen over time and stop responding to standard MS therapies. So far, there are no inmunomodulatory treatment available to stop or reverse this form of MS.

Primary Progressive (PPMS) affects about 15% of MS patients; these patients have gradually worsening manifestations from the onset without clinical relapses, patients with PPMS tend to be older, have fewer abnormalities on brain MRI, and generally do not respond to standard MS therapies. About 15% of patients have PPMS from the onset. So far, there are no inmunomodulatory treatment available to stop or reverse this form of MS.

Progressive Relapsing (PRMS) entails gradual neurologic worsening from the onset with subsequent superimposed relapses. PPMS is suspected to represent SPMS, in which the initial relapses were unrecognized, forgotten, or clinically silent.

Interferon beta 1a, Interferon beta 1b and glatiramer acetate have failed to demonstrate efficacy in slowing down the disability progression. Therapies such as mitoxantrone, methotrexate, azatioprine and cyclophosphamide have poor methodological clinical studies where both RRMS patients are evaluated together with SP and PPMS patients, and do not show a reduction in the progression of disability. Finally, there is no evidence with natalizumab, fingolimod and teriflunomide; however, unpublished data would indicate no effect on the progressive forms. Therefore, current available drugs, including the disease modifying drugs used for RRMS, cannot reverse, halt or even slow down the progressive disability in the SP & PPMS forms.

Interferon beta-1a (IFNB-1a) has been tested for efficacy in Secondary progressive MS (SPMS). This testing included two clinical trials. The IMPACT study included a total of 436 subjects with Secondary progressive MS with relapses that were randomized to receive IFNB-1a weekly (intramuscular) or placebo for two years. The IMPACT data showed a significant benefit in the group of IFNB-1a in terms of MSFC decrease (40.4%, p=0.033), fewer relapses (33%, p=0.008), better outcome in eight of eleven MS Quality of Life scales and less MRI activity (p<0.001).

The SPECTRIMS study included a total of 618 patients with Secondary progressive MS with relapses who received IFNB-1a (three times weekly) or placebo for 3 years. The data showed that IFNB-1a did not significantly affect disability progression (p=0.146), although significant treatment benefit was observed on relapse rate (reduced from 0.71 to 0.50 per year, p<0.001) and on MRI outcomes.

Interferon beta-1b (IFNB-1b) has also been tested for efficacy in Secondary progressive MS in two clinical trials. In the EUSPMS: a total of 718 patients with Secondary progressive MS were randomized to IFNB-1b or placebo with treatment duration of up to three years. The EUSPMS data showed that the time to confirmed 1.0 point progression on the Expanded Disability Status Scale (EDSS) was delayed (p=0.007) and the progression of 2.0 EDSS point was 27% lower.

The NASPMS study included 939 subjects with Secondary progressive MS with relapses that were randomized to either placebo or IFNB-1b. The NASPMS data showed no treatment benefit on time to confirmed progression of disability, though relapse and MRI-related outcomes showed significant benefit. A combined analysis of both the EUSPMS and NASPMS trials shows that the patients with more pronounced disability progression and continuing relapse activity could be more likely to benefit from treatment.

For Primary progressive MS (PPMS), a Cochrane systematic review included two randomized controlled trials (entailing a total of 123 patients), and compared interferon treatment versus placebo in patients with PPSM. This review did not show differences regarding the proportion of patients with progression of the disease (RR 0.89, 95% CI 0.55 to 1.43), and it was associated with a greater frequency of treatment-related adverse events (RR 1.90, 95% CI 1.45-2.48). One of the trials showed a lower number of active MRI lesions at two years in interferon arm (difference −1.3, 95% CI −2.15 to −0.45, P=0.003).

Glatiramer Acetate was tested in a controlled clinical trial (Wolinsky 2007) wherein a total of 943 patients with PPMS were randomized. The data showed there was a non-significant delay in time to sustained accumulated disability (hazard ratio, 0.87 [95% confidence interval, 0.71-1.07]; p=0.1753).

In La Mantia 2010 (the Cochrane systematic review), data for 1049 patients with Primary progressive MS contributed to the meta-analysis. No benefit was shown in SPMS and PPMS patients. No major toxicity was found. The most common systemic adverse event was a transient and self-limiting patterned reaction of flushing, chest tightness, sweating, palpitations, and anxiety. Local injection-site reactions were observed in up to a half of patients treated with glatiramer acetate, thus making a blind assessment of outcomes questionable.

Mitoxantrone was evaluated in Hartung (2002), describing a controlled clinical trial of 194 patients with worsening RRMS or SPMS with relapses. Patients were assigned placebo or mitoxantrone; 188 patients completed the protocol and were able to be assessed at 24 months. At 24 months, the mitoxantrone group experienced benefits compared with the placebo group on different clinical measures (difference 0.3 [95% CI 0.17-0.44]; p<0.001), reducing progression of disability and clinical exacerbations.

Similarly, Martinelli (2005), the Cochrane systematic review, provides a meta-analysis of four clinical trials involving a total of 270 patients with RRMS, PRMS and SPMS with relapses. Meta-analysis showed that mitoxantrone reduced the progression of disability at 2 years follow-up (proportion of patients with 6-months confirmed progression of disability: Odds Ratios 0.3, p=0.05). These results, however, are based on heterogeneous trials in terms of drug dosage and inclusion criteria.

Cyclophosphamide was meta-evaluated in La Mantia (2007), a Cochrane systematic review. The meta-analysis included four RCTs comparing Cyclophosphamide to placebo or no treatment, entailing a total of 152 participants. The meta-analysis showed that cyclophosphamide did not prevent the long-term (12, 18, 24 months) clinical disability progression as defined as evolution to a next step of EDSS score. However, the mean change in disability (final disability subtracted from the baseline) significantly favoured the treated group at 12 (effect size −0.21, 95% confidence interval −0.25 to −0.17) and 18 months (−0,19, 95% confidence interval −0.24 to −0.14) but favoured the control group at 24 months (0.14, CI 0.07 to 0.21).

Methotrexate was studied in a trial with 60 progressive MS patients only. The results from Gray (2006) show there was a non-significant reduction in sustained EDSS progression and number of relapses in favour of methotrexate therapy. There were no data on relapse rate and no difference in time to first relapse. Minor side effects were reported in both methotrexate (87.1%) and placebo groups (89.7%), but there were no major side effects.

Rituximab was studied in 439 PPMS patients, randomized to intravenous rituximab or placebo. The data from Hawker (2009) showed differences in time to confirmed disease progression between rituximab and placebo did not reach significance (96-week rates: 38.5% placebo, 30.2% rituximab; p=0.14). From baseline to week 96, rituximab patients had less (p<0.001) increase in T2 lesion volume; brain volume change was similar (p=0.62) to placebo. Adverse events were comparable between groups.

The Azathioprine Cochrane systematic review (Casetta (2007)) included 698 randomized patients with all clinical forms of MS. The pooled data showed azathioprine reduced the number of patients who had relapses during the first year of treatment (relative risk reduction [RRR]=20%; 95% CI=5% to 33%), at two years (RRR=23%; 95% CI=12% to 33%) and three years (RRR=18%; 95% CI=7% to 27%) follow-up. These results were consistent in sensitivity analysis. There was no heterogeneity among the studies. Data from only three small trials with a total of 87 patients were available to calculate the number of patients who progressed during the first two to three years. There was a statistically significant benefit (RRR=42%; 95% CI=7% to 64%) of azathioprine therapy at three years' follow-up; this result was robust after sensitivity analyses.

The prior art thus teaches many potential therapies for MS. The art, however, also teaches that certain forms of MS remain resistant to any currently-known therapy.

Andrographolide (the claimed compound) and certain analogous compounds are taught by Juan Luis HANCKE et al., U.S. Pat. No. 8,080,495. That patent also teaches autoimmune diseases including "rheumatoid diseases, psoriasis, systemic dermatomycocytis, multiple sclerosis [and] lupus erythematosus." See 1:29-39. Regarding multiple sclerosis, the patent says, "Using the mixture of andrographolides described in Example 9, normalization in the symptoms of the disease occurs following 3 months of treatment of the composition of the present invention. In addition, the composition does not interfere with other treatments." See 18:10-15. The patent unfortunately does not expressly say what form of multiple sclerosis was there studied. Mention of "other treatments," however, means that the form of MS there studied must have been the only one which in fact has "other treatments," i.e., relapsing-remitting form MS. This patent thus fails to expressly nor implicitly teach use of andrographolide to treat any progressive form of MS.

Further, the art teaches that every other treatment for relapsing-remitting MS is ineffective for progressive forms of MS. See supra. Thus, this prior art patent failed to provide the skilled artisan a reasonable expectation of success in using the claimed compounds for any progressive form of MS.

Published PCT Application WO2013/096423 teaches the claimed compounds synergistically improve the efficacy of interferon in treating Multiple Sclerosis. See page 2 at Summary, page 8 at 7$^{th}$ paragraph. The art, however, teaches that interferons are not effective at all to treat progressive forms of MS. See supra. Thus, the skilled artisan would have read WO '423 to teach combining interferon with the claimed compounds to treat the relapsing-remitting form of MS, rather than a progressive form of MS. Similarly, the artisan would have read WO '423 to teach that interferon is an indispensable part of MS therapy.

BRIEF SUMMARY

We have tested andrographolide in a controlled, randomized, double-blinded human clinical trial of andrographolide 140 mg orally administered twice per day (i.e., 280 mg per day) in patients with progressive forms of Multiple Sclerosis. The principle objective of that study was to determine efficacy, safety and tolerability of andrographolide in retarding the progression of brain atrophy. Secondary end-points included: delay in the disability capacity progression through the Expanded Disability Status Scale (EDSS) and Multiple Sclerosis Funcitonal Composite (MSFC) at 24 months compared to the baseline; delay in cognitive impairment by means of Paced Auditory Serial Addition Test (PASAT), Symbol Digit Modalities Test (SDMT) and depression (Beck) at 24 months compared to the baseline; quality of life Multiple Sclerosis Impact Scale (MSIS 29) and fatigue (Krupp) through parameters reported by the patients at 24 months compared to the baseline; Tolerability of andrographolide measured by Magnetic Resonance (MR) at 24 months compared to baseline; Number and volume of new lesions or larger size in T2 by MR at 24 months compared to the baseline; Number of new hipointense lesions in T1 or (gadolinium captive) by MR at 24 months compared to baseline; Delay in the retinal thinning measured by Optical Coherence Tomography (OCT) and visual field at 24 months compared to the baseline; and Safety of andrographolide at 24 months through the record of adverse effects in symptom diary and programmed interviews. The details of the study are described more completely in U.S. Provisional patent application Ser. No. 62/347,218 (filed 8 Jun. 2016), incorporated here by reference.

BRIEF DESCRIPTION OF THE DRAWINGS

FIG. 1 shows in vitro results. (A) Lymph node cell suspensions obtained from C57BL/6 and BALB/c mice were co-cultured with increasing concentrations of IB-MS for 72 h. After this time, supernatants were harvested and analyzed for IL-2 release by ELISA assay (circles) and T cell proliferation (squares) was determined by Cell Titer assay. (B) Mice treated with vehicle (solid circles) or andrographolide (empty circles) were MOG-immunized one week later and clinical score determined daily. These data indicate that IB-MS treatment interferes with T cell activation and prevents EAE.

FIG. 3 shows inflammatory infiltrate and demyelination is reduced in spinal cord of AG-treated mice. MOG-immunized C57BL/6J mice (150 ug MOG-peptide; 500 ug MT; 200 ng PT) were treated daily with 4 mg/kg andrographolide. Animals were treated at the beginning of chronic phase (day 15 post-immunization) until day 20 post-immunization. As controls MOG-immunized C57BL/6J mice were injected with vehicle (PBS) daily. At day 21 p.i. mice were sacrificed. MOG-immunized mice treated with either PBS (A-C) or AG (B-D) were perfussed and 4% p-formaldehyde fixed. Toraxic spinal cords sections were dissected and analyzed for inflammatory infiltrate by hematoxylin-eosin staining (H&E) and for demyelination with luxol fast blue staining (LFB). Insets show higher magnification (20×).

FIG. 10 shows the effect of andrographolide (A) on 9-HPT in human patients. The numbers (x axis) on the figure are measurements 6: corresponds to 2 year treatment. There are still many patients that need to complete the 2 year treatment. The data therefore show a lot of variance. Despite that, we can see that the treated patients are more skilled and more quickly complete the task of upper extremely function. The 9-HPT is a brief, standardized, quantitative test of upper extremity function. It is the second component of the MSFC to be administered at each visit. Both the dominant and non-dominant hands are tested twice. The patient is seated at a table with a small, shallow container holding nine pegs and a wood or plastic block containing nine empty holes. On a start command when a stopwatch is started, the patient picks up the nine pegs one at a time as quickly as possible, puts them in the nine holes, and, once they are in the holes, removes them again as quickly as possible one at a time, replacing them into the shallow container. The total time to complete the task is recorded. Two consecutive trials with the dominant hand are immediately followed by two consecutive trials with the non-dominant hand.

FIG. 11 shows MSIS 29 scale results for human patients. In control group (b) one can see that the patients after 2 years as compared to day 0, the percentage goes from 95 to 75, meaning a physical & psychological deterioration. In the treatment group (a), the percentage goes from 80 to 90. Preliminarily, it shows that the treatment patients maintain or slightly improve their scores.

DETAILED DESCRIPTION

The details of our clinical study are described in U.S. Provisional patent application Ser. No. 62/347,218 (filed 8 Jun. 2016), incorporated here by reference. While that study was designed as a 24-month study, interim results after only 12 months of treatment show statistically-significant efficacy. Our interim results show that in the treatment of Secondary Progressive (SP) and Primary Progressive (PP) forms of Multiple Sclerosis (MS), remyelination, and neurogenesis are stimulated by oral administration of andrographolide-class compounds.

There are 3 components of the Multiple Sclerosis Functional Composite (MSFC) disease activity index: function of the legs, function of the arms and cognitive function. The corresponding tests are a 25 feet (7.6 m) walk; test of 9 holes and pin and the Paced Auditory Serial Addition test 3 (PASAT3). Multiple attempts will be made of each test in each visit. The MSFC score and the scores of the 3 sub-scales and the change from the basal values will be recorded in each visit One measure of progressive MS disease severity is the Expanded Disability Status Scale (EDSS). EDSS is a scale to determine the neurological disability in MS and is used to confirm progression of the disease. It consists of a system of two parts. The first part measures eight functional systems (FS). The second part measures disability on a scale of 1 to 10, zero being no disability and 10 being death due to MS.

Literature shows that in non-treated MS patients, the evaluated disability by EDSS increases one point in the 15% of the subjects after 2 years of follow up (Kragt et al, 2010). The size of the sample in order to evaluate a reduction in 50% of this parameter is expected in the intervened group, 7.5% of the subjects increases one point in the disability scale. In order to find differences with a level of significance of 0.05 and a potency of 0.80, it will be necessary to evaluate 28 subjects per group. Considering also that one intervened subjects for each control and a 20% percentage of drop off, the total number of subjects to evaluate is 68. To find differences with a level of significance of 0.05 and a potency of 0.80 it is necessary to evaluate 28 subjects per group. Considering also one intervened subject for each control and a 20% "drop off", the total number to evaluate is 68.

Figure 1A:
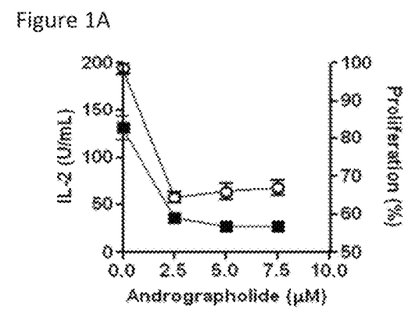
Figure 1B:
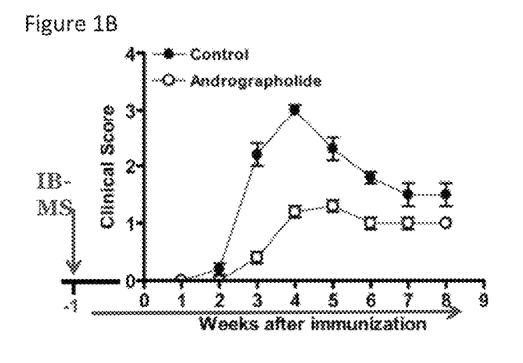
Figure 2:
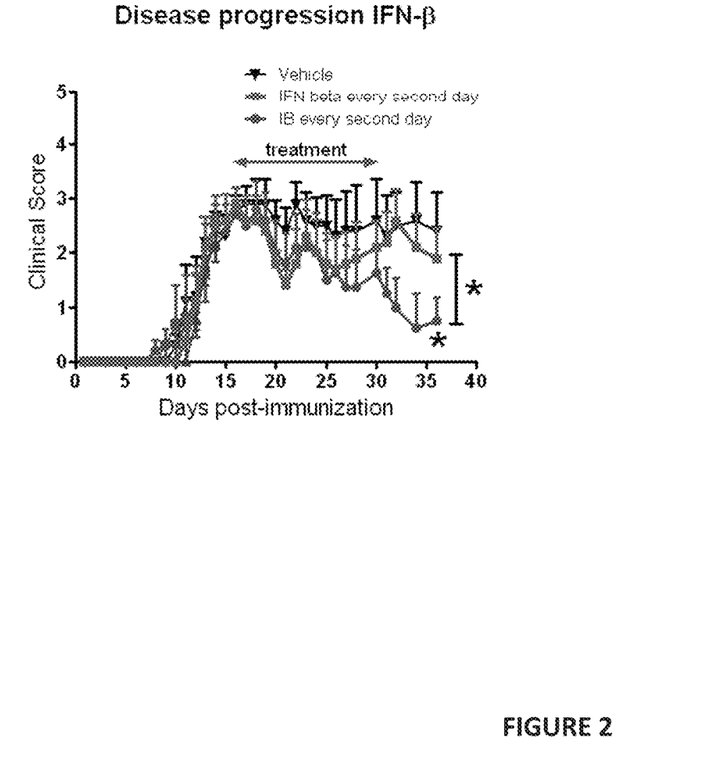
FIG. 2 shows the comparative effect between IB-MS and IFN-β-treatment on three groups of MOG-immunized C57BL/6J mice (150 ug MOG-peptide; 500 ug MT; 200 ng PT) were treated every second day with PBS (black triangles), IFN-β (purple squares) or 4 mg/kg IB (blue circles) at the beginning of chronic phase (day 15 post-immunization) until day 30 post-immunization. These data indicate that IB-MS has a therapeutic effect in EAE.
Figure 3:
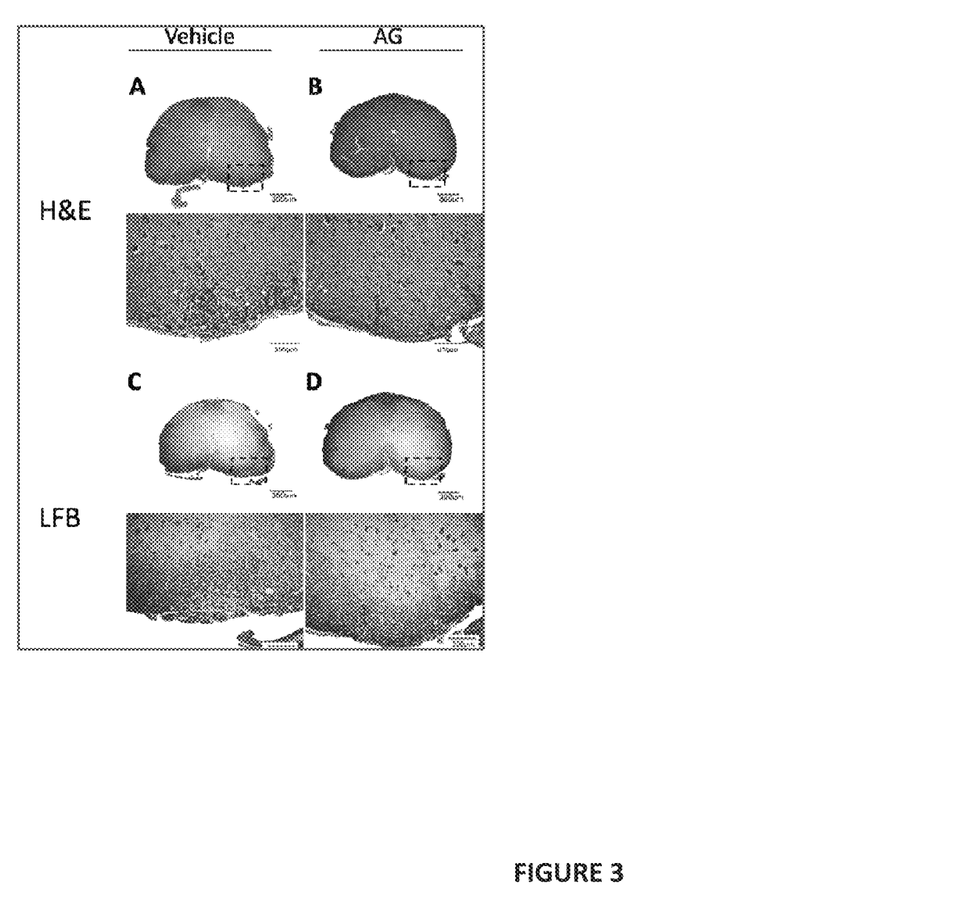
Figure 4:
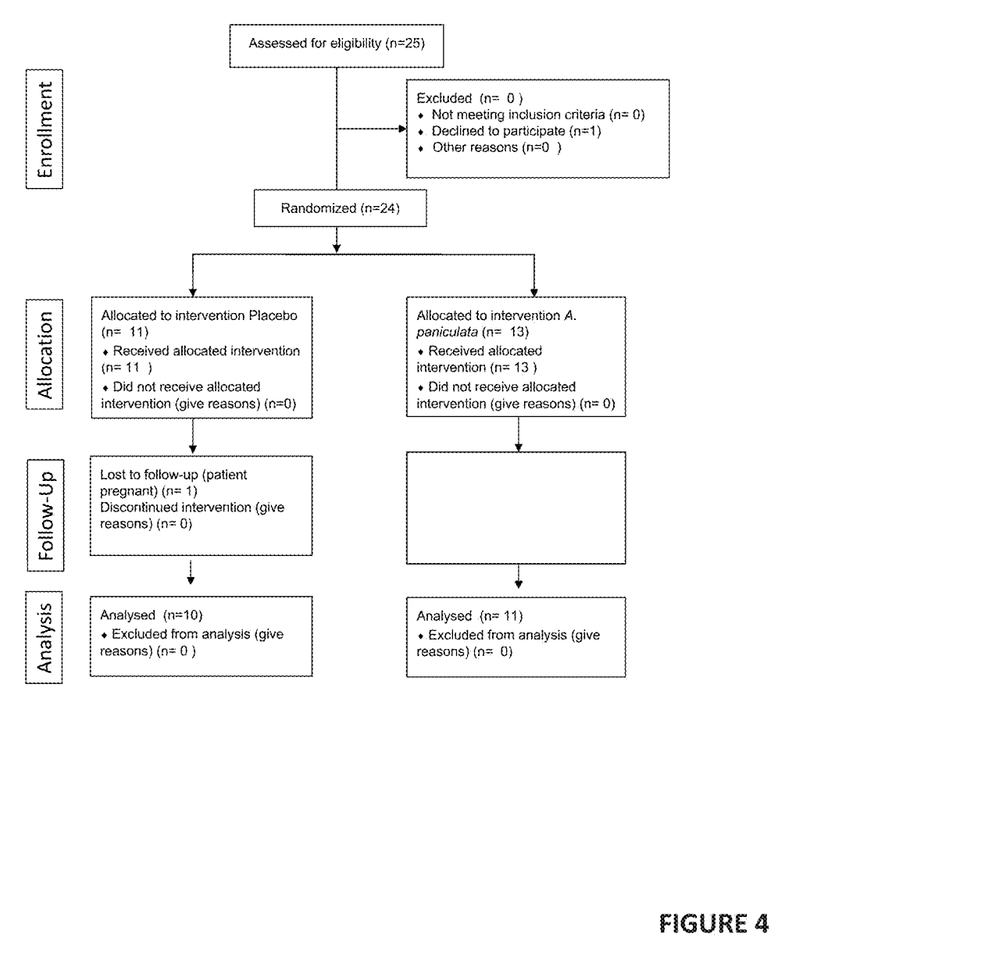
FIG. 4 illustrates the process flowchart for our 12-month pilot clinical study.
Figure 5:
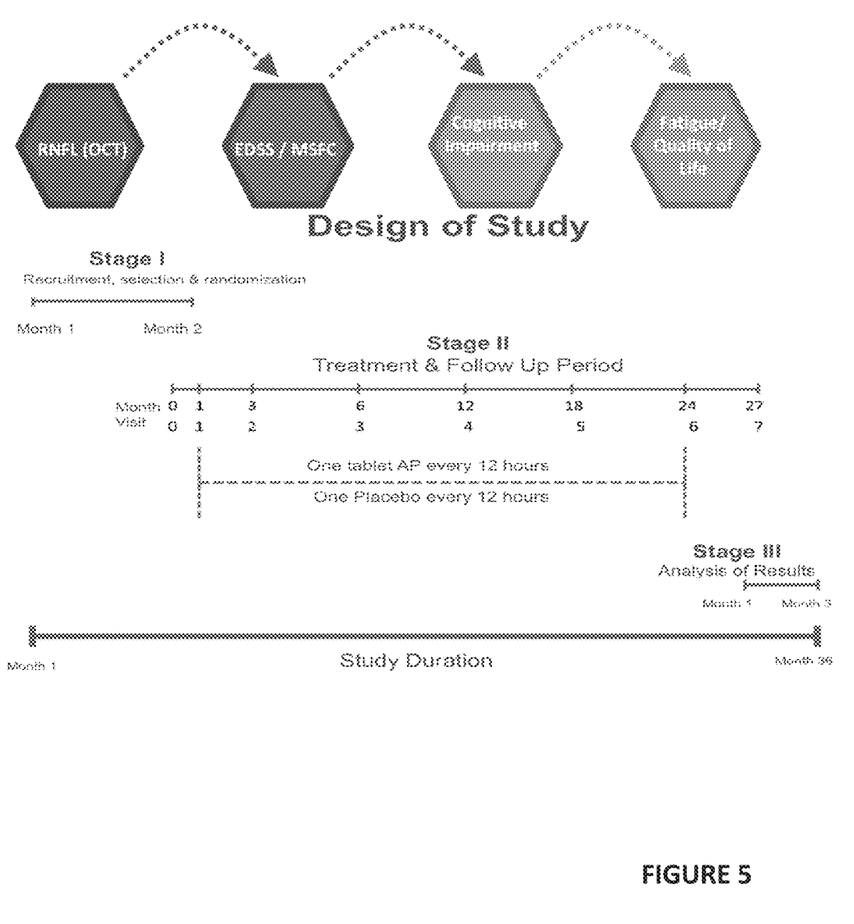
FIG. 5 lists certain secondary outcomes and provides the study timeline.
Figure 6:
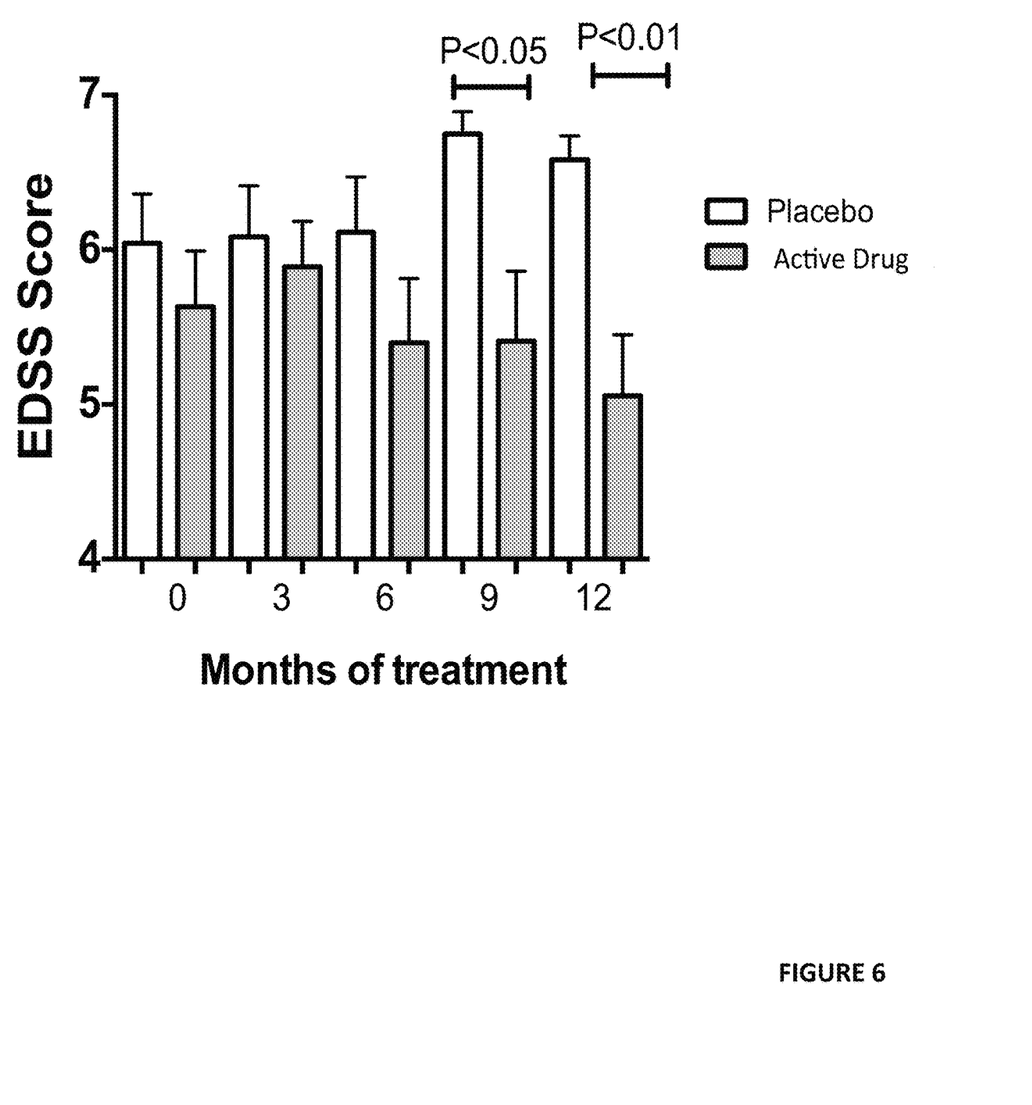
FIG. 6 presents the effect of IR-MS on Expanded Disability Status Scale (EDSS) in patients with progressive MS.

Our results for 12 months of treatment are provided in FIG. 6. FIG. 6 shows that treatment provides an improvement viz placebo which becomes statistically-significant by nine months and more significant by twelve months of treatment.

Figure 7:
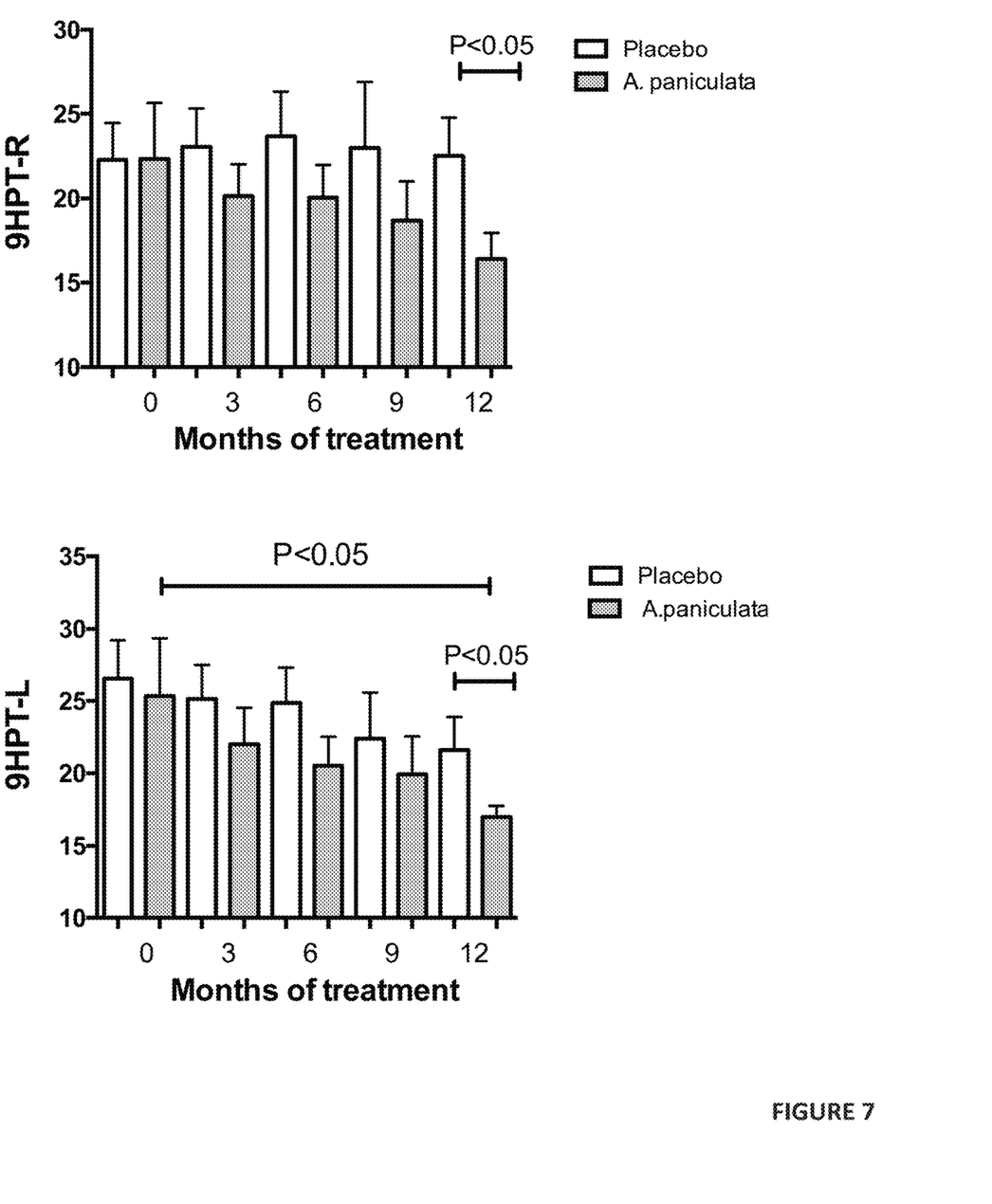
FIG. 7 presents the effect of IB-MS on the Nine Hole Pin Test (9HPT) (L=left handed; R=right handed) in patients with progressive MS.

The Nine Hole Pin Test (9HPT) is a component of the MS Functional Composite (MSFC) score. 9HPT is a timed test measuring the time (seconds) required to insert each of nine pins into nine holes in a plank. The test is done on each of the right and left arms. The test measures eye-hand coordination and fine muscle control. Our results for twelve months of treatment are provided in FIG. 7. Results for the right hand test (9HPT-R) show treatment provides an improvement (reduction) in time required to complete the test, which improvement becomes statistically significant by twelve months of treatment. The data for the left hand test (9HPT-L) confirm this improvement, yet curiously shows the improvement becomes statistically significant almost immediately and grows in significance over twelve months. Note that in comparing the left and right hand data, the vertical (time) scale for the left hand test is compressed. This is because the left hand is generally non-dominant, thus requiring systematically longer times to completion.

Another measure of coordination is the 25-Feet Walk Test (25 FWT). The 25 FWT measures the time (seconds) required to walk a distance of 7.6 meters (25 feet). Literature shows that in non-treated MS patients, disability evaluated by time (seconds) (time a patient takes to cover a distance of 25 feet), increases one point in 45% of the subjects (Kragt et al, 2010). Sample size was calculated to evaluate a reduction in 50% in this parameter (that is, it is expected that in the intervened group a 22.5% of the subjects increases one point in the disability scale). In order to find a difference in the level of significance of 0.05 and a potency of 0.80 it is necessary to evaluate 68 subjects per group. Considering also one intervened subject for each control and a 20% of drop off, the total number of subjects to evaluate is 68. In order to find a difference with a level of significance of 0.05 and a potency of 0.43, it is necessary to evaluate 28 subjects per group. Considering also one intervened subjects for each control and a 20% drop off, the total subjects to evaluate is 68.

Figure 8:
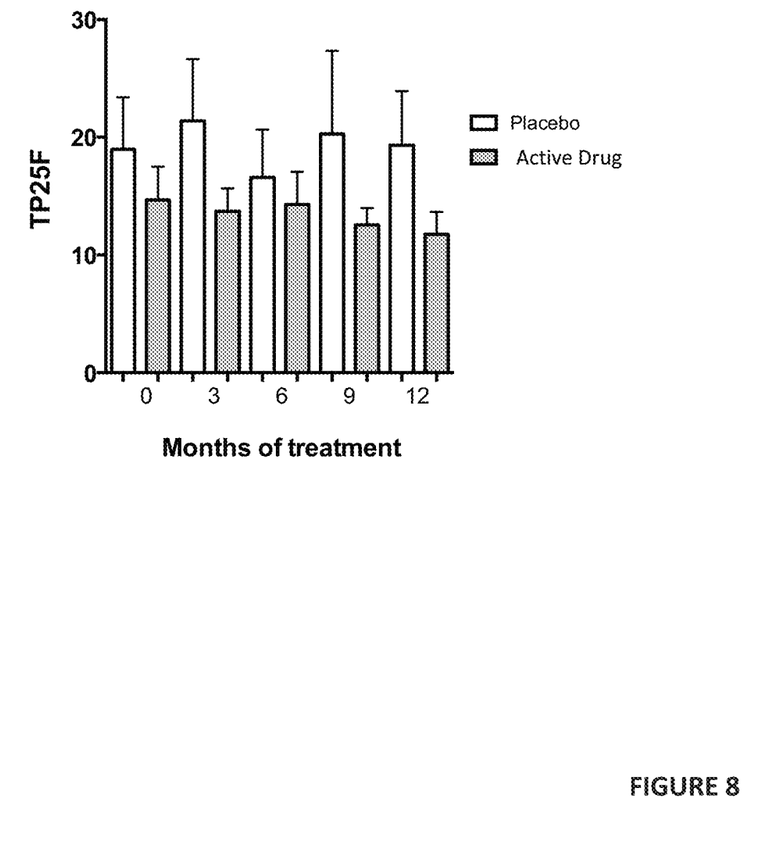
FIG. 8 presents effect of IB-MS on a 25-Feet Walk Test (25 FWT) in patients with progressive MS.

Our preliminary data in FIG. 8 show that treatment provides an improvement (reduction) in time required to complete the test viz placebo, which improvement becomes statistically significant immediately on commencement of treatment and persists for twelve months of treatment, Thus, an object of the present invention is to provide pharmaceutical compositions for treating Secondary Progressive (SP) and Primary Progressive (PP) forms of Multiple Sclerosis (MS), compromising oral administration of andrographolide and or analogues thereof, optionally including one or more pharmaceutically-acceptable excipients and/or carriers.

Another object of the present invention is, therefore, to provide a method of treating a subject suffering from SPMS and PPMS and/or another demyelinating disease, the method consisting of administering the pharmaceutical compositions of the invention to the subject in an effective amount and for a time sufficient to produce remyelination and neurogenesis.

The present invention provides pharmaceutical compositions for treating SPMS and PPMS forms and/or other demyelinating diseases, comprising a compound of Formula (I):

(I)

wherein $R_1$ is selected from the group consisting of hydrogen, alkyl or hydroxyl, $R_2$ is selected from the group consisting of hydroxyalkyl or alkyl-O-$L_1$, wherein $L_1$ is a carbohydrate moiety, $R_3$ is selected from the group consisting of hydrogen or hydroxyl, X is selected from the group consisting of C(=$CH_2$), CH(OH), or a 2,2-dimethyloxirane;

Z is selected from the group consisting of $CH_2$, CH(OH) or C(=O), and $R_4$ is selected from the group consisting of an optionally substituted $L_2$-alkyl or $L_2$-alkenyl, wherein $L_2$ is an optionally substituted 3-furanyl or 3-fur-3-enyl moiety, or a pharmaceutically acceptable salt, ester, ether or prodrug thereof, and one or more pharmaceutically acceptable excipients and/or carriers.

In one embodiment, $R_1$ is methyl.

In another embodiment, $R_2$ is hydroxymethyl or $CH_2$—O-Glc, wherein Glc is a glycoside-forming glucose moiety.

In another embodiment, $R_4$ is optionally substituted 3-(3-furanyl)-propyl, 3-(3-furanyl)-prop-1-enyl, 3-(3-furanyl)-prop-2-enyl, 3-(3-fur-3-enyl)-propyl or 3-(3-fur-3-enyl)-prop-1-enyl wherein the 3-furanyl or the 3-fur-3-enyl moieties are further optionally substituted.

In one embodiment, $R_1$, $R_2$, $R_3$, X and Z are those described above, and $R_4$ is selected from the group consisting of:

-continued wherein:

$R_5$ is selected from the group consisting of hydrogen or hydroxyl,

$R_6$ and $R_7$ are independently selected from the group consisting of hydrogen, hydroxyl, or alkyloxy, or $R_6$ and $R_7$ are simultaneously replaced by a single direct bond between the carbon atoms denoted by *, thus forming a dimer of two monomer molecules of formula (I), and $R_8$ and $R_9$ are independently selected from the group consisting of hydrogen, hydroxyl or alkyloxy.

In one embodiment, $R_6$, $R_7$, $R_8$ or $R_9$ can be independently methoxy.

In preferred embodiments, the compounds of Formula (I) are selected from the group consisting in andrographolide, neoandrographolide, 14-deoxyandrographolide14-deoxy-11,12-didehydroandrographolide, andrographiside, andrograpanin, 14-deoxy-11-oxo-andrographolide, 14-deoxy-11-hydroxy-andrographolide, 14-deoxy-12-hydroxy-andrographolide, 3,14-dideoxyandrographolide, 3-oxo-14-deoxyandrographolide, 8,17-epoxy-14-deoxyandrographolide, 14-deoxy-17-beta-hydroxyandrographolide, 12-hydroxyandrographolide, bisandrographolide A, 3-oxo-14-deoxy-11,12-didehydroandrographolide, 7-hydroxy-14-deoxyandrogapholide,15-methoxy-3,19-dihydroxy-8(17)11,13-ent-labda-trien-16,15-olide, andropanolide, 14-deoxy-12-methoxy-andrographolide, 14-epi-andrographolide, 19-hidroxi-ent-labda-8(17),13-dien-15,16-olide, 3,13,14,19-tetrahydroxy-ent-labda-8(17),11-dien-16,15-olide, 3,19-dihydroxy-15-methoxy-ent-labda-8(17),11,13-trien-16,15-olide, and 3,19-dihydroxy-ent-labda-8(17),12-dien-16,15-olide, For example, our invention entails treating a progressive form of MS by administering andrographolide without accompanying interferon. Alternatively, one may combine andrographolide with interferon.

Andrographolide (or AP) is the principal active component responsible for most of the biological activities attributed to *Andrographis paniculata*, a medicinal plant traditionally used in Asian countries such as China, India, Malaysia for the treatment of common cold, dysentery, fever, amygdalitis, hepatic diseases (Panossian, Davtyan et al. 2002; C. Patarapanich 2007; S. K. Mishra 2007). The traditional use and pharmacological studies of *Andrographis paniculata* have been previously well documented (Nemoto 2008).

Andrographolide

AP is a diterpenic lactone that is present mainly in the leaves, relatively easily to extract whose molecular structure has been determined (A. B. Smith III 1982). This compound has a manifold of biological effects including cytotoxic effect intumoral cells, anti-angiogenic, anti-inflammatory and immune modulating effects. AP inhibits selectively the proliferation of different types of tumoral cells (Cheung, Cheung et al. 2005; Kim, Hwi et al. 2005; Zhou, Zhang et al. 2006; Geethangili, Rao et al. 2008; Shi, Lin et al. 2008; Wang 2008; Zhao, He et al. 2008; Zhou, Lu et al. 2008; Yang, Wu et al. 2009), by means of inducing apoptosis, necrosis, through the induction of apoptosis, necrosis, arrest cell cycle or cell differentiation and suppression of angionenic factors such the endotelial vascular growth factor (VEGF) and inhibitor of metaloproteinases (TIMP-1) (Sheeja, Guruvayoorappan et al. 2007). For this reason, AP has the potential as an agent for the treatment (Rajagopal, Kumar et al. 2003; Jada, Subur et al. 2007) and HIV infection (Calabrese, Berman et al. 2000). Clinically, AP has demonstrated efficacy in Rheumatoid Arthritis (Burgos, Hancke et al. 2009), some types of cancer (See, Mason et al. 2002) and common cold (Caceres, Hancke et al. 1997).

One of the potent effects of AP is it anti-inflammatory and immune modulatory activity. AP has the capacity to induce a significant stimulation of the protective immune response in vivoagainst infectious and oncogenic agents (Puri, Saxena et al. 1993; Kumar, Sridevi et al. 2004; Khan 2007). Among the anti-inflammatory effect, there is a decrease in the production of oxygen reactive molecules, the inhibition of the expression of pro-inflammatory enzymes de enzymes such as COX-2 and iNOS (Chiou, Lin et al. 1998; Chiou, Chen et al. 2000) and inhibition of the activation transcriptional factor NF-☐B (Wang, Liu et al. 2004; Xia, Ye et al. 2004; Hidalgo, Romero et al. 2005; Iruretagoyena, Tobar et al. 2005).

In a mice model, we have previously demonstrated that AP decreases: 1) the maturation of dendritic cells and its capacity to present antigens to T cells, interfering with the activation of the transcription factor NF-kB (Hidalgo, Romero et al. 2005); 2) the process of activation of Jurkat cell line (lymphom of T cells) though the inhibition of the activation of the transcription factor NFAT and transductions signals pathways MAPK-Erk 1/2 (Carretta, Alarcon et al. 2009). Besides, AP could have an effect on neurodegeneration mediated by inflammation, since AP reduces reactive oxygen species, TNF-α, nitric oxide and prostaglandins $E_2$ in microglia (Wang, Liu et al. 2004). The anti-inflammatory and immune modulatory of AP has been demonstrated in inflammatory diseases in vivo in different models such as arthritis (Burgos, Hancke et al. 2009), lupus and asthma (Kalergis, Iruretagoyena et al. 2009). In a EAE model, we have reported that the prophylactic administration of AP prevents the development Of EAE through the inhibition of T and B cells response against myelin antigens (Iruretagoyena, Tobar et al. 2005). Many clinical studies have shown that AP is well tolerated and safe.

Considering the anti-inflammatory and immune modulatory antecedents of AP and the molecular basis that underlie the inflammatory process of MS, we postulate that this compound is a potential treatment for MS.

Figure 9:
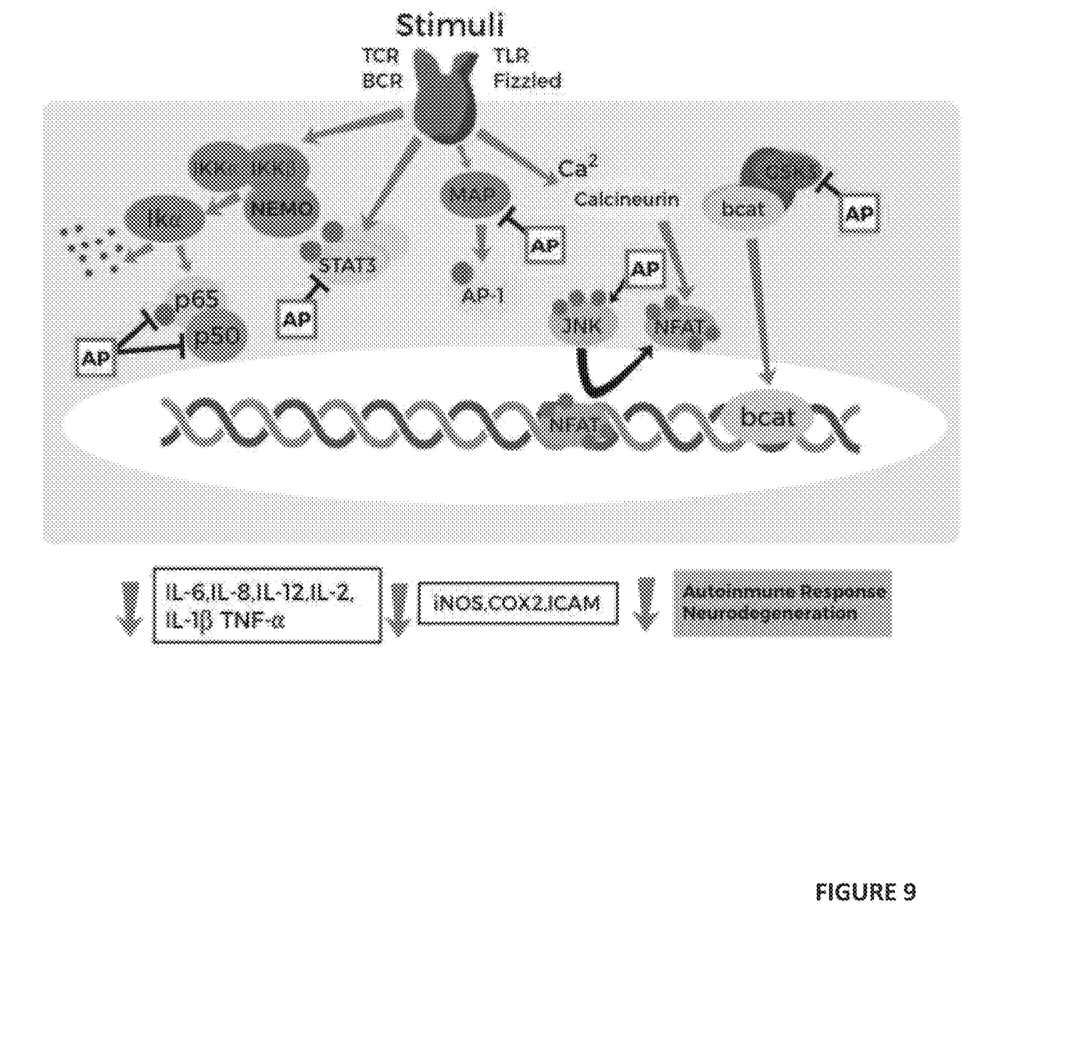
FIG. 9 presents a schematic diagram of possible mechanisms of action at the cellular level of our invention (AP=andrographolide).
Figure 10:
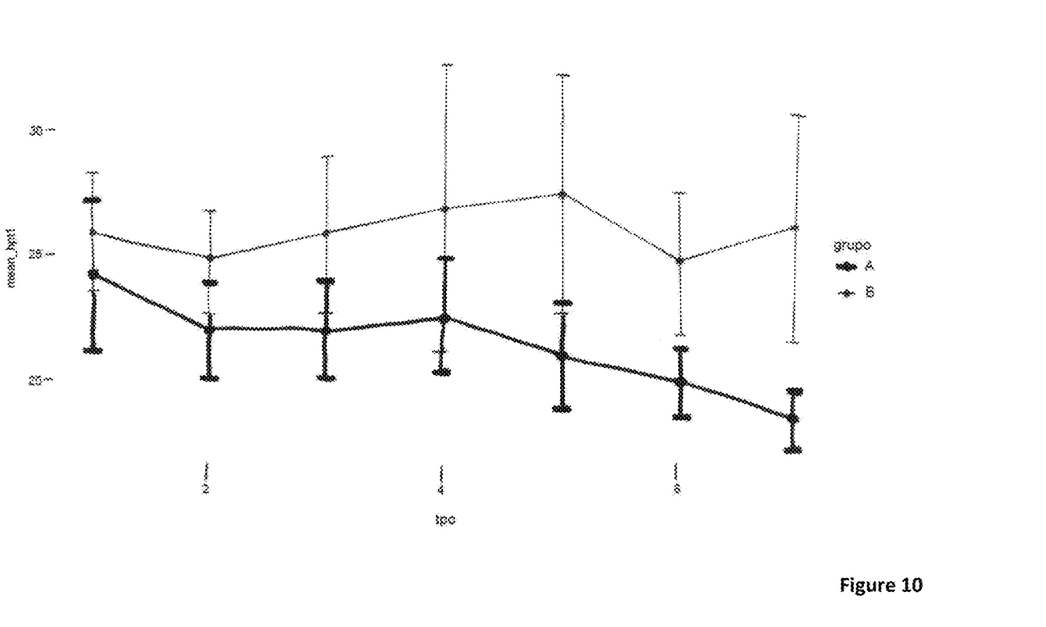
Figure 11:
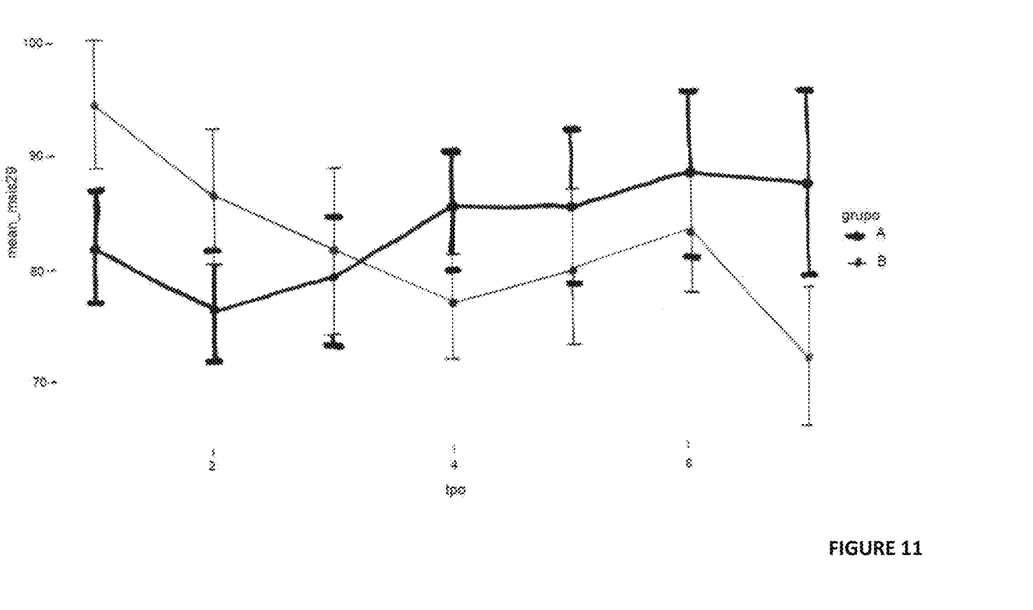

Given our disclosure here, the artisan can readily derive variants of it. For example, FIG. 9 presents a schematic diagram of possible mechanisms of action and cellular level binding sites of andrographolide. The artisan may thus employ analogs of andrographolide which provide a similar mechanism of action, to produce similar effects. Alternatively, the artisan may vary the dosage amount to provide an equivalent therapeutic effect. While our actual experiments used solid tablets, hard gelatin capsules, liquid extracts and other oral dosage forms would be expected to function equivalently. We thus intend the legal coverage of our patent to be defined not by our specific examples, but by the legal claims appended here as approved by The Patent Office, and legally-permissible equivalents thereof.

I claim:

1. A method of treating a human patient comprising: administering, to a human patient diagnosed with a Progressive form of multiple sclerosis, an oral dosage form comprising a comprising a compound of Formula (I):

wherein $R_1$ is selected from the group consisting of hydrogen, alkyl or hydroxyl, $R_2$ is selected from the group consisting of hydroxyalkyl or alkyl-O-$L_1$, wherein

$L_1$ is a carbohydrate moiety,

$R_3$ is selected from the group consisting of hydrogen or hydroxyl,

X is selected from the group consisting of C(=$CH_2$), CH(OH), or a 2,2-dimethyloxirane, Z is selected from the group consisting of $CH_2$, CH(OH) or C(=O), and $R_4$ is selected from the group consisting of:

wherein:
R₅ is selected from the group consisting of hydrogen or hydroxyl,
R₆ and R₇ are independently selected from the group consisting of hydrogen, hydroxyl, or alkyloxy, or R₆ and R₇ are simultaneously replaced by a single direct bond between the carbon atoms denoted by *, thus forming a dimer of two monomer molecules of Formula (I), and
R₈ and R₉ are independently selected from the group consisting of hydrogen, hydroxyl or alkyloxy,
or a pharmaceutically acceptable salt or ester thereof;
said oral dosage form providing an amount of said compound of Formula I effective to slow the progression of a Progressive form of multiple sclerosis in a human patient diagnosed with Progressive multiple sclerosis.

2. The method of claim 1, wherein said amount effective comprises about 240 mg of said compound per day.

3. The method of claim 1, wherein said amount effective is effective to slow progression of said Progressive form of multiple sclerosis as measured using an assay comprising an assay selected from the group consisting of: the Expanded Disability Status Scale, the 9-Hole Pin Test, the 25-Feet Walk Test and the Multiple Sclerosis Functional Composite index.

4. The method of claim 1, wherein said progressive form of multiple sclerosis is selected from the group consisting of: Primary Progressive Multiple Sclerosis, Secondary Progressive Multiple Sclerosis and Progressive Relapsing Multiple Sclerosis.

5. The method of claim 1, wherein said compound of Formula (I) comprises a compound selected from the group consisting of: andrographolide, neoandrographolide, 14-deoxyandrographolide, 14-deoxy-11,12-didehydroandrographolide, andrographiside, andrograpanin, 14-deoxy-11-oxo-andrographolide, 14-deoxy-11-hydroxy-andrographolide, 14-deoxy-12-hydroxy-andrographolide, 3,14-dideoxyandrographolide, 3-oxo-14-deoxyandrographolide, 8,17-epoxy-14-deoxyandrographolide, 14-deoxy-17-beta-hydroxy-andrographolide,12-hydroxyandrographolide, bisandrographolide A, 3-oxo-14-deoxy-11,12-didehydroandrographolide, 7-hydroxy-14-deoxyandrographolide,15-methoxy-3,19-dihydroxy-8(17)11, 13-ent-labda-trien-16,15-olide, andropanolide, 14-deoxy-12-methoxy-andrographolide, 14-epi-andrographolide, 19-hydroxy-ent-labda-8(17),13-dien-15,16-olide, 3,13,14,19-tetrahydroxy-ent-labda-8(17),11-dien-16,15-olide, 3,19-dihydroxy-15-methoxy-ent-labda-8(17),11,13-trien-16,15-olide and 3,19-dihydroxy-ent-labda-8(17),12-dien-16,15-olide.

6. The method of claim 1, further comprising: administering interferon to said patient.

* * * * *